US012678089B2

(12) United States Patent
Nagatani et al.

(10) Patent No.: US 12,678,089 B2
(45) Date of Patent: Jul. 14, 2026

(54) SIGNAL PROCESSING APPARATUS AND SIGNAL PROCESSING METHOD

(71) Applicants: Pixie Dust Technologies, Inc., Tokyo (JP); Shionogi & Co., Ltd., Osaka (JP)

(72) Inventors: Yoshiki Nagatani, Tokyo (JP); Kazuki Takazawa, Tokyo (JP); Koichi Ogawa, Osaka (JP); Kazuma Maeda, Osaka (JP)

(73) Assignees: Pixie Dust Technologies, Inc., Tokyo (JP); Shionogi & Co., Ltd., Osaka (JP)

( * ) Notice: Subject to any disclaimer, the term of this patent is extended or adjusted under 35 U.S.C. 154(b) by 772 days.

(21) Appl. No.: 18/170,254

(22) Filed: Feb. 16, 2023

(65) Prior Publication Data

US 2023/0190173 A1     Jun. 22, 2023

Related U.S. Application Data

(63) Continuation of application No. PCT/JP2022/039423, filed on Oct. 24, 2022.

(30) Foreign Application Priority Data

Oct. 25, 2021     (JP) ................................. 2021-173635

(51) Int. Cl.
　　*A61B 5/374*　　(2021.01)
　　*G10H 7/02*　　(2006.01)
(52) U.S. Cl.
　　CPC .............. *A61B 5/374* (2021.01); *G10H 7/02* (2013.01); *G10H 2250/645* (2013.01)
(58) Field of Classification Search
　　CPC .......... A61B 5/374; A61B 5/486; G10H 7/02; G10H 2250/645; G10H 1/08; G10H 2220/376; G10K 15/02; G16H 40/63; G16H 20/70; A61M 2021/0027; A61M 2021/005; A61M 2205/3584; A61M 2205/505;

(Continued)

(56) References Cited

U.S. PATENT DOCUMENTS 5,337,752　A　*　8/1994　Reeves ..................... A61B 7/00
　　　　　　　　　　　　　　　　　　　　600/513
10,159,816　B2　*　12/2018　Tsai ....................... A61M 21/00
10,265,497　B2　　4/2019　Tsai et al.
(Continued)

FOREIGN PATENT DOCUMENTS

AU　　　2018390085　A1　*　7/2020　........... A61B 5/4872
JP　　　57032497　A　　2/1982
(Continued)

OTHER PUBLICATIONS

International Search Report issue on Dec. 20, 2022, in corresponding International Patent Application No. PCT/JP2022/039423, 4 pages.

(Continued)

*Primary Examiner* — Oyesola C Ojo
(74) *Attorney, Agent, or Firm* — Maier & Maier, PLLC

(57) ABSTRACT

A signal processing apparatus receives an input acoustic signal, acquires a first acoustic signal having a periodic variation corresponding to the frequency of gamma waves, and outputs an output acoustic signal based on the acquired first acoustic signal and the second acoustic signal. The second acoustic signal is based on the input acoustic signal.

20 Claims, 18 Drawing Sheets

(58) Field of Classification Search
CPC ............ A61M 21/00; A61M 2205/581; A61M
2230/10; G10L 21/0364
See application file for complete search history.

(56) References Cited

U.S. PATENT DOCUMENTS

| | | | | |
|---|---|---|---|---|
| 10,279,192 | B2 * | 5/2019 | Malchano | .......... A61N 1/36132 |
| 10,293,177 | B2 | 5/2019 | Malchano et al. | |
| 10,307,611 | B2 | 6/2019 | Malchano et al. | |
| 10,682,490 | B2 | 6/2020 | Tsai et al. | |
| 10,702,705 | B2 | 7/2020 | Malchano et al. | |
| 10,843,006 | B2 | 11/2020 | Malchano et al. | |
| 11,141,604 | B2 | 10/2021 | Malchano et al. | |
| 11,241,586 | B2 | 2/2022 | Tsai et al. | |
| 2015/0223743 | A1 * | 8/2015 | Pathangay | ............... A61B 5/18 600/509 |
| 2016/0324433 | A1 * | 11/2016 | Tan | ...................... A61N 1/3925 |
| 2019/0246992 | A1 * | 8/2019 | Volpe | ................. A61N 1/37282 |
| 2019/0387998 | A1 * | 12/2019 | Garten | ................. A61M 21/00 |
| 2020/0316334 | A1 | 10/2020 | Tsai et al. | |
| 2020/0316335 | A1 | 10/2020 | Tsai et al. | |
| 2021/0121713 | A1 | 4/2021 | Malchano et al. | |
| 2021/0386300 | A1 * | 12/2021 | Rogers | ............... A61B 5/02055 |
| 2022/0233879 | A1 | 7/2022 | Tsai et al. | |
| 2023/0001127 | A1 * | 1/2023 | Khalil | ................... A61M 21/00 |

FOREIGN PATENT DOCUMENTS

| | | | |
|---|---|---|---|
| JP | 60073694 | A | 4/1985 |
| JP | 04296200 | A | 10/1992 |
| JP | 05344599 | A | 12/1993 |
| JP | 2020014716 | A | 1/2020 |
| JP | 2020501853 | A | 1/2020 |
| WO | 2021108460 | A1 | 6/2021 |

OTHER PUBLICATIONS

Martorell et al., "Multi-sensory Gamma Stimulation Ameliorates Alzheimer's-Associated Pathology and Improves Cognition" Elsevier BV, Cell. Apr. 4, 2019 177(2): 256-271.e22., doi:10.1016/j.cell.2019.02.014, 40 pages.

* cited by examiner

[FIG. 1]
1
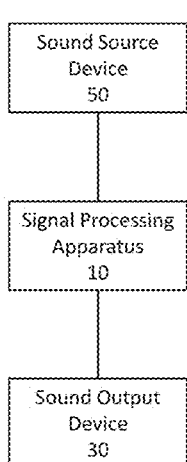

[FIG. 2]
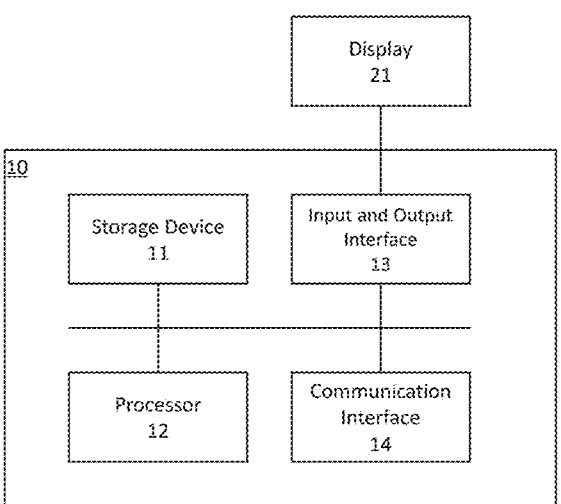

[FIG. 3]
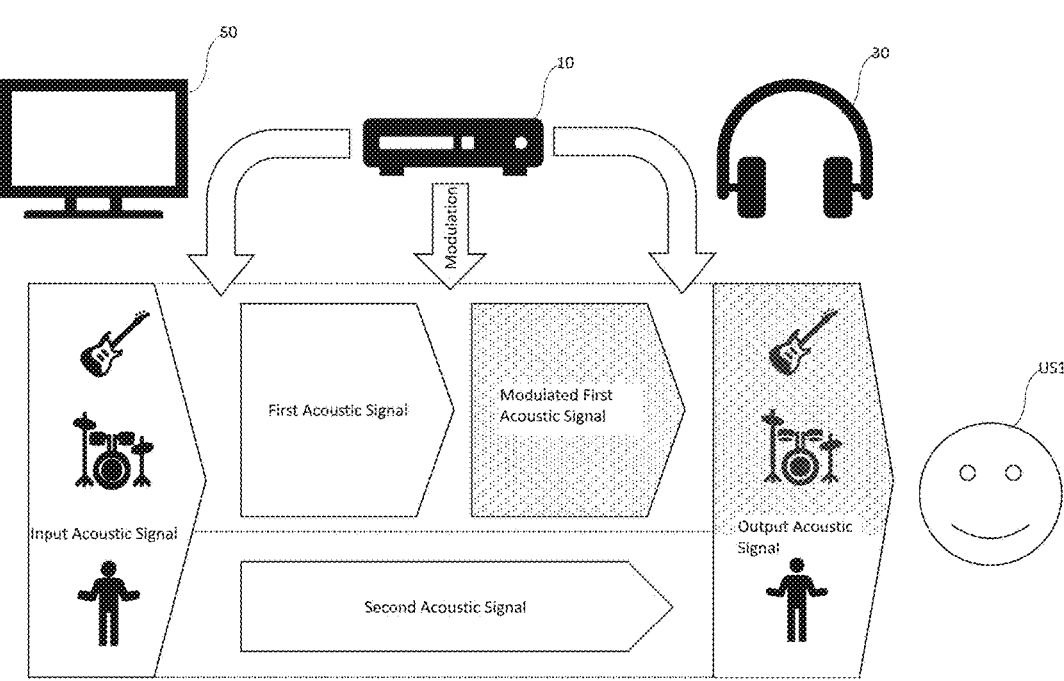

[FIG. 4]
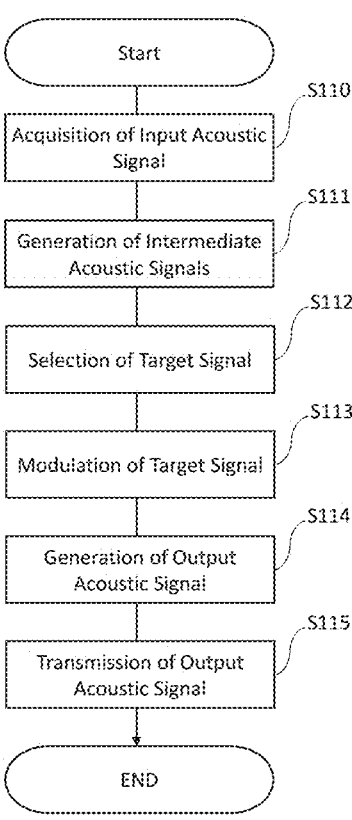

[FIG. 5]
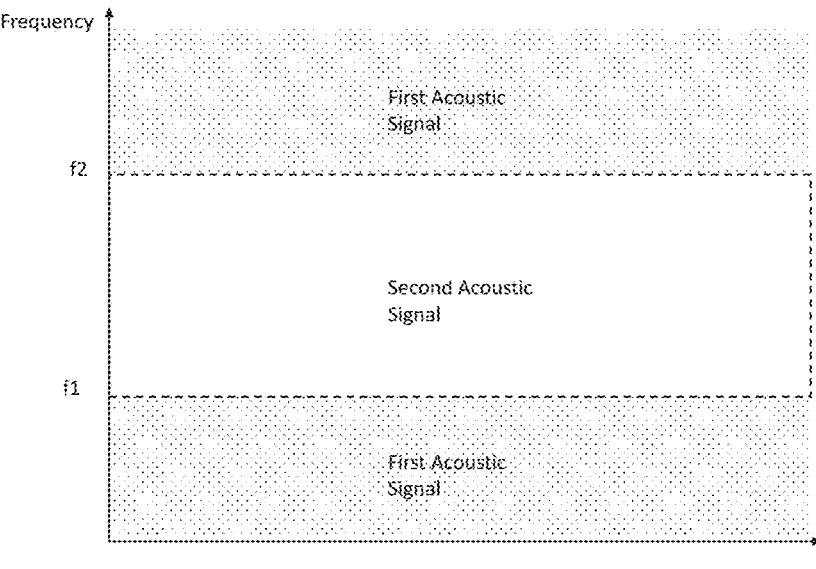

[FIG. 6]
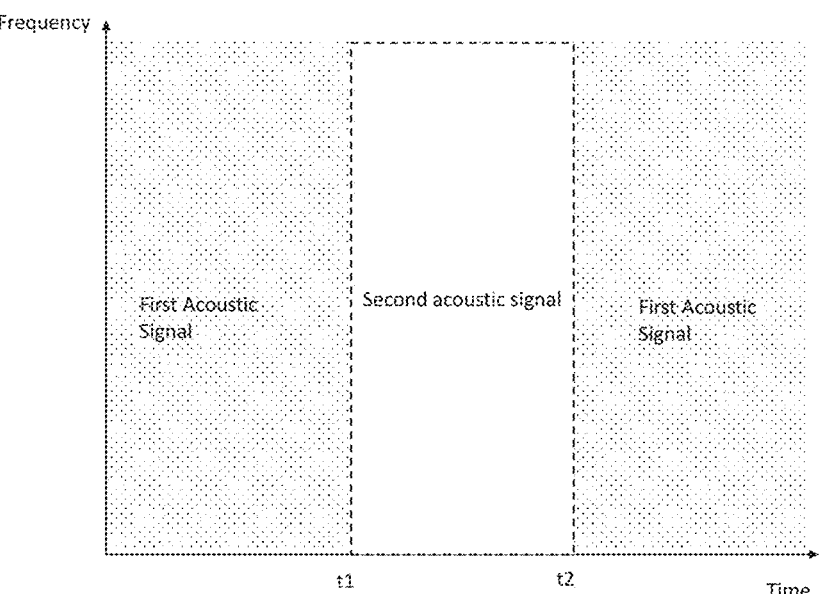

[FIG. 7]
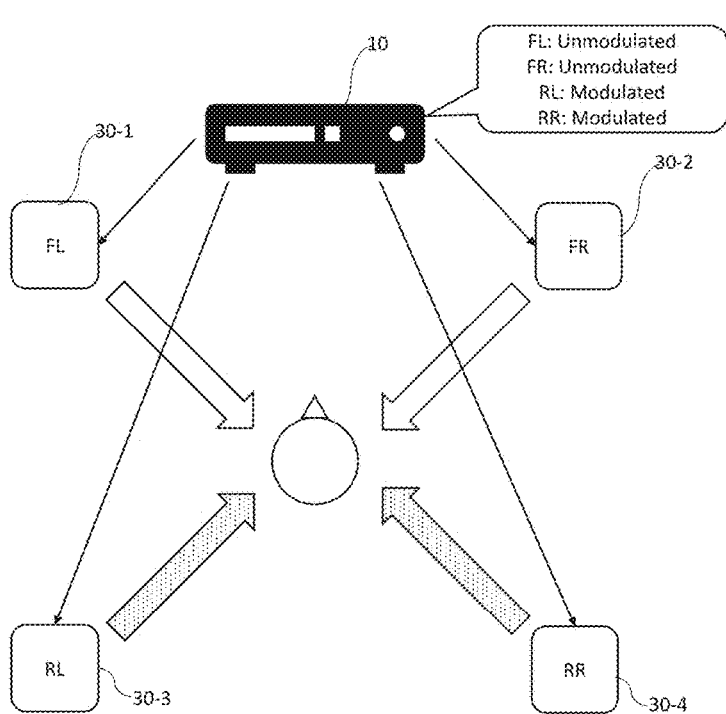

[FIG. 8]
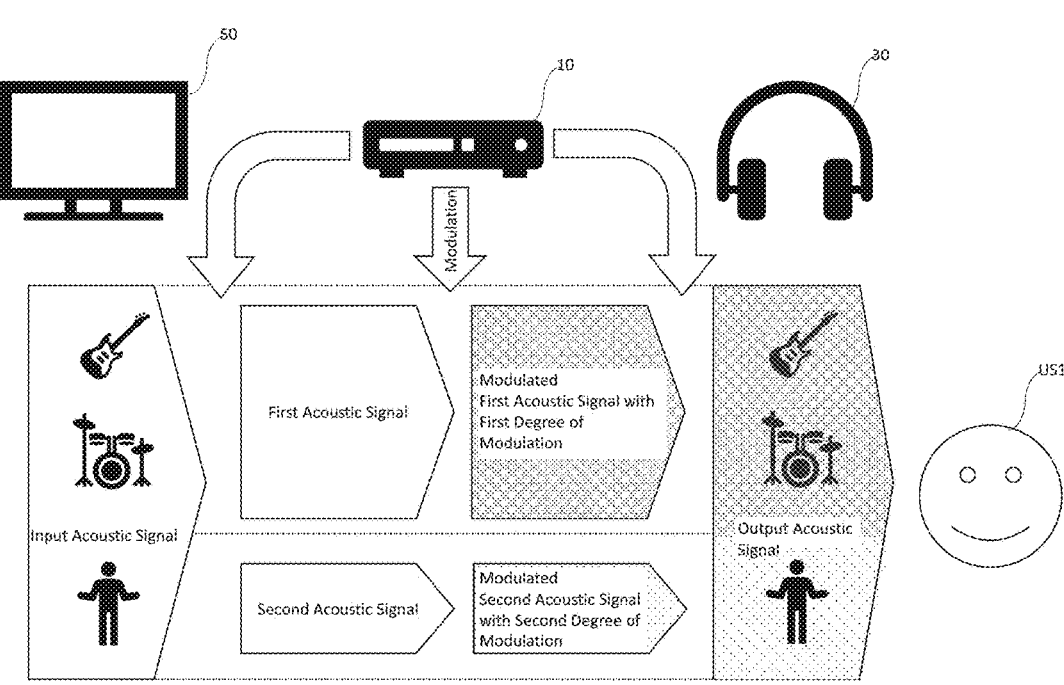

[FIG. 9]
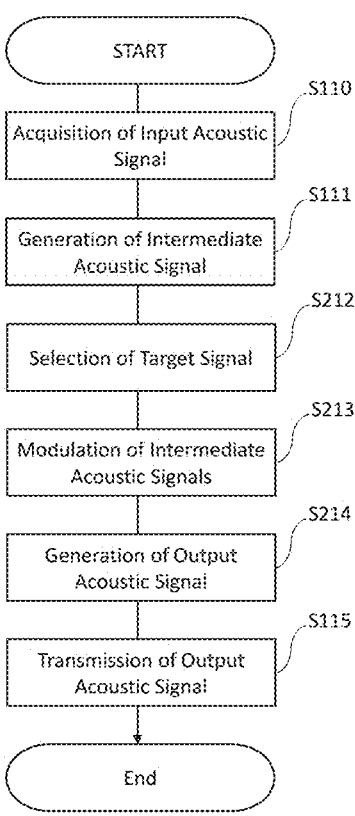

[FIG. 10]
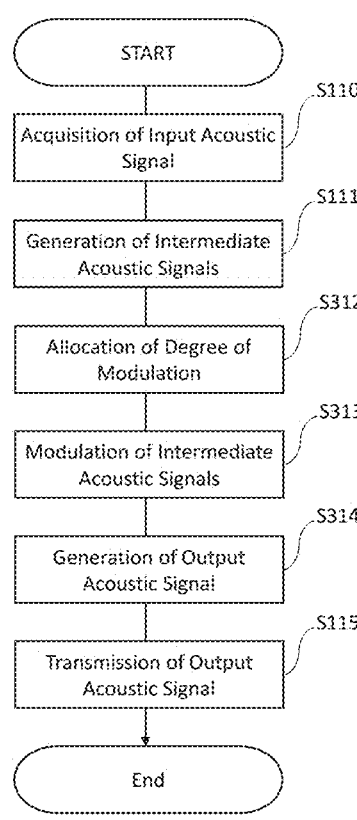

[FIG. 11]
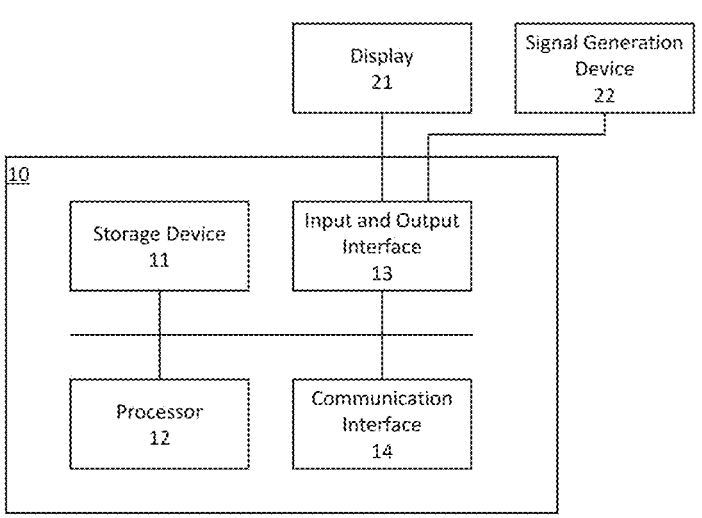

[FIG. 12]
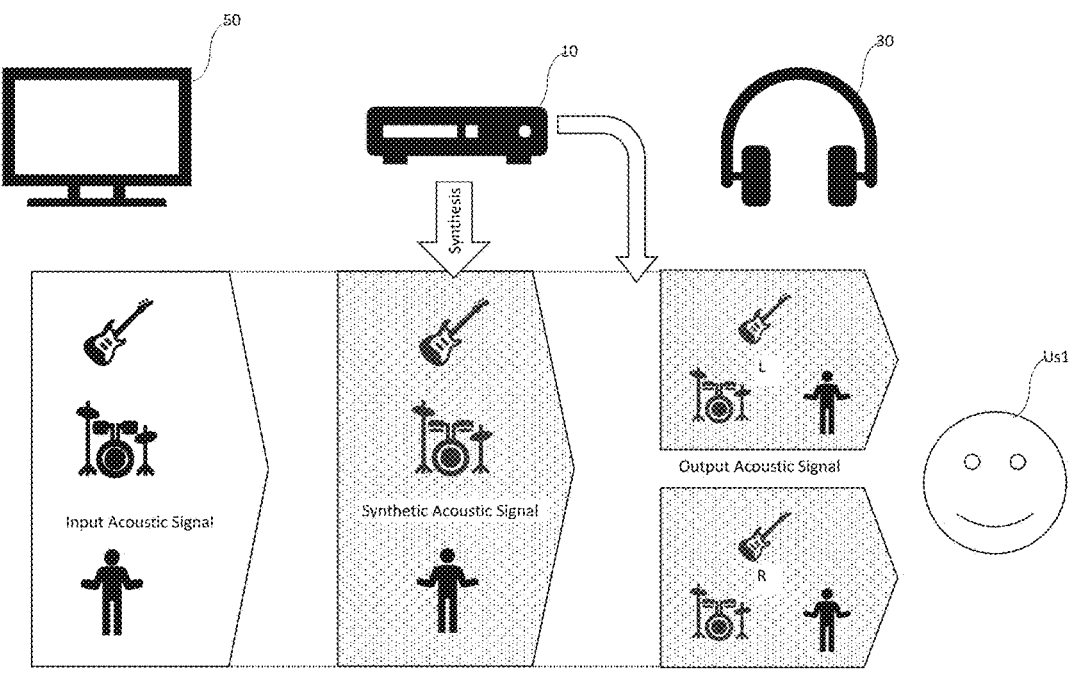
Input Acoustic Signal
Synthetic Acoustic Signal
Synthesis
Output Acoustic Signal

[FIG. 13]
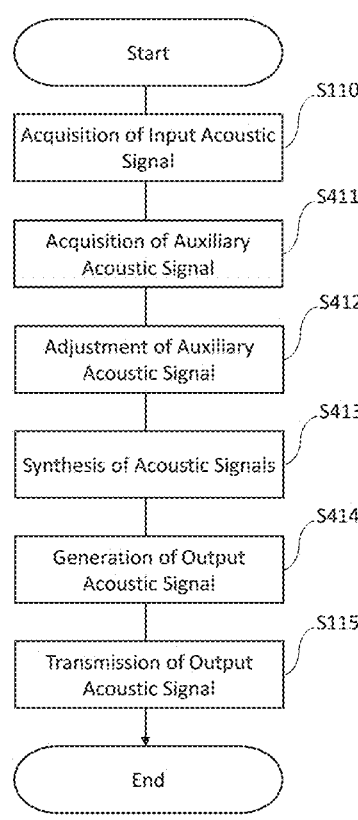

[FIG. 14]
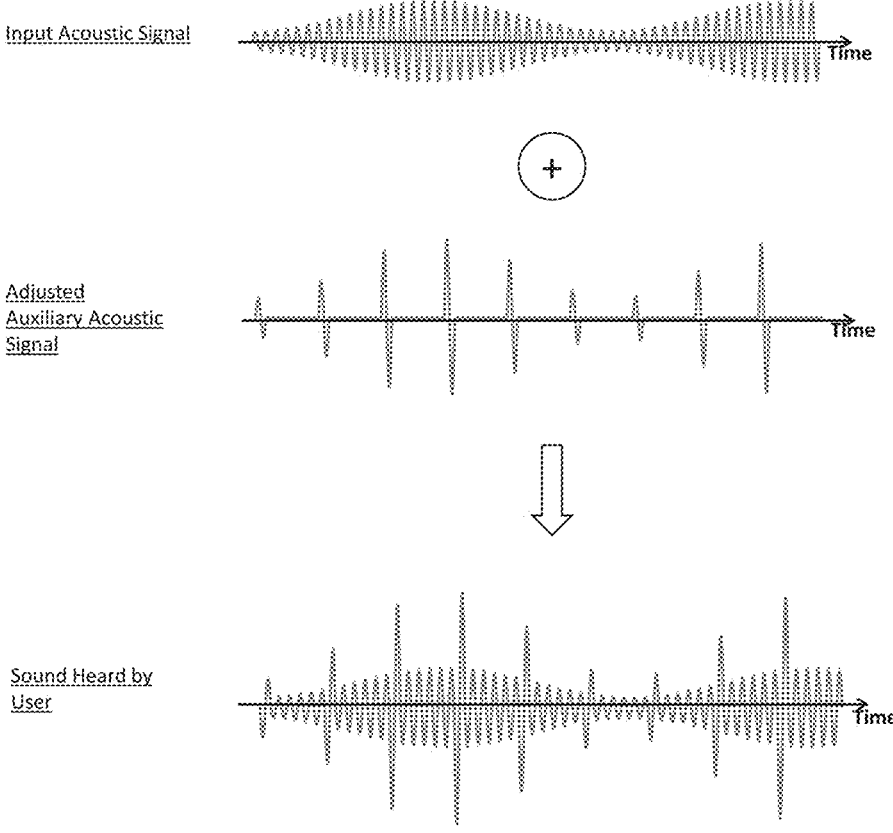

[FIG. 15]
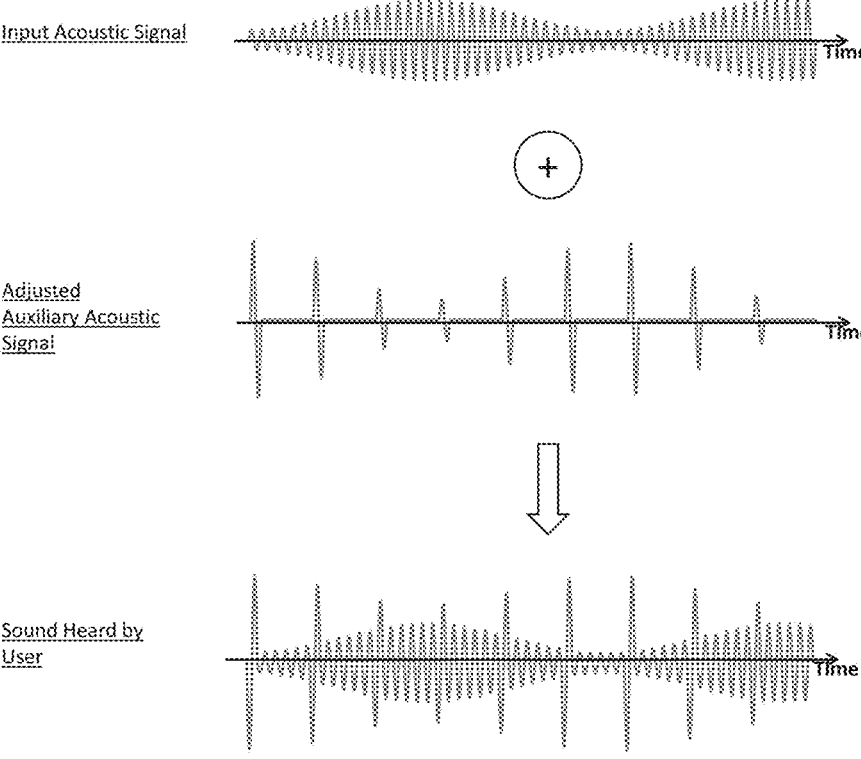

[FIG. 16]
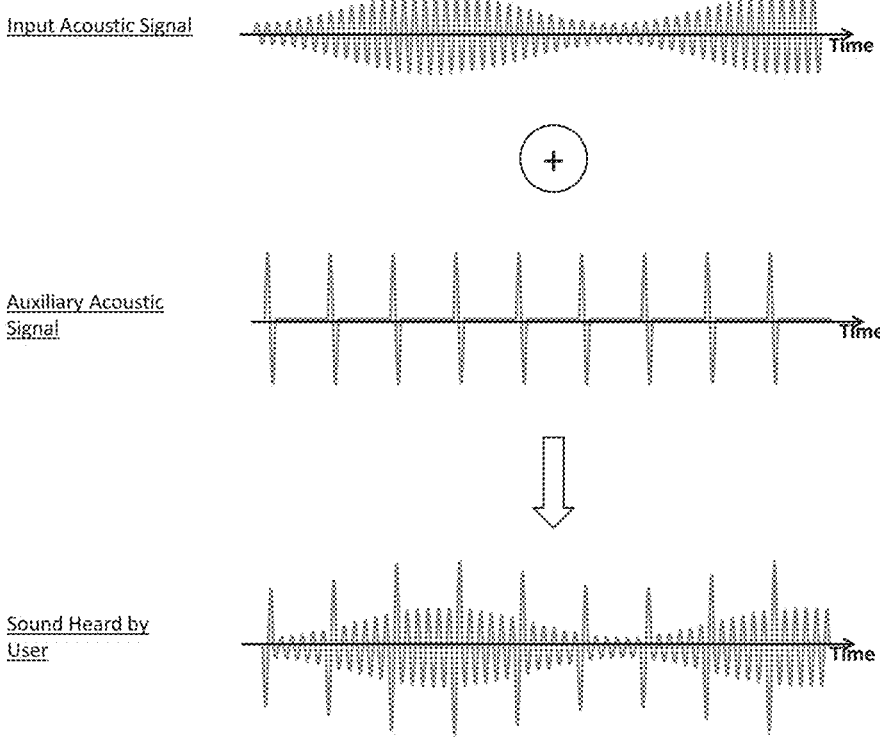

[FIG. 17]
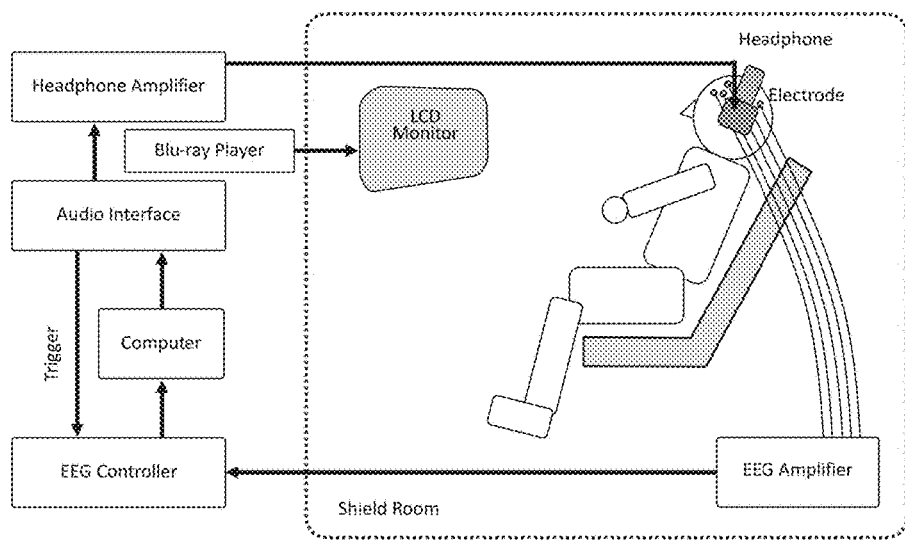

[FIG. 18]
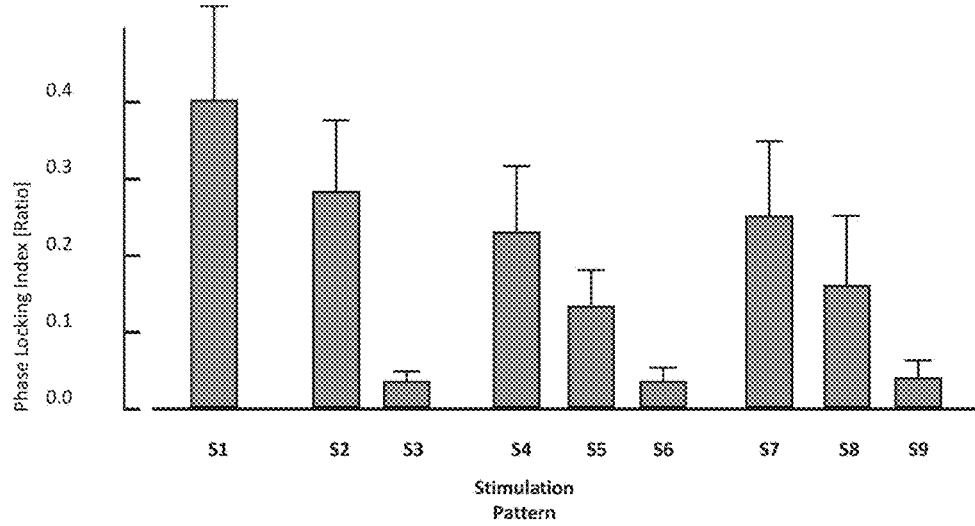

SIGNAL PROCESSING APPARATUS AND SIGNAL PROCESSING METHOD

CROSS-REFERENCE TO RELATED APPLICATION

This application is a Continuation Application of No. PCT/JP2022/39423, filed on Oct. 24, 2022, and the PCT application is based upon and claims the benefit of priority from Japanese Patent Application No. 2021-173635, filed on Oct. 25, 2021, the entire contents of which are incorporated herein by reference.

TECHNICAL FIELD

The present disclosure relates to a signal processing apparatus, and a signal processing method.

BACKGROUND

There is a research report that when an organism is made to perceive a pulsed sound stimulus at a frequency of about 40 times per second to induce gamma waves in the brain of the organism, it is effective in improving the cognitive function of the organism (see Literature 1: Multi-sensory Gamma Stimulation Ameliorates Alzheimer's-Associated Pathology and Improves Cognition Cell 2019 Apr. 4; 177 (2):256-271.e22. doi: 10.1016/j.cell.2019.02.014.).

Gamma waves refer to those whose frequency is included in the gamma band (25 to 140 Hz) among nerve vibrations obtained by capturing periodic nerve activity in the cortex of the brain by electrophysiological techniques such as electroencephalograms and magnetoencephalography.

Japanese Patent Application Publication No. 2020-501853 discloses adjusting the volume by increasing or decreasing the amplitude of sound waves or soundtracks to create rhythmic stimulation corresponding to stimulation frequencies for inducing brain wave entrainment.

However, when the amplitude of the acoustic signal is increased or decreased, it may become difficult for the listener to hear the information contained in the acoustic signal (for example, singing, announcements, etc.). That is, increasing or decreasing the amplitude of the acoustic signal can detract from the listener's acoustic experience.

BRIEF DESCRIPTION OF DRAWINGS

FIG. 1 is a block diagram showing the configuration of an acoustic system according to a first embodiment;

FIG. 2 is a block diagram showing the configuration of the signal processing apparatus of the first embodiment;

FIG. 3 is an explanatory diagram of one aspect of the first embodiment;

FIG. 4 is a diagram showing the overall flow of acoustic signal processing by the signal processing apparatus of the first embodiment;

FIG. 5 is an explanatory diagram of frequency characteristics of an acoustic signal;

FIG. 6 is an illustration of temporal characteristics of an acoustic signal;

FIG. 7 is an explanatory diagram of characteristics of output of an acoustic signal;

FIG. 8 is an explanatory diagram of one aspect of modification 1;

FIG. 9 is a diagram showing an overall flow of acoustic signal processing by the signal processing apparatus of modification 1;

FIG. 10 is a diagram showing an overall flow of acoustic signal processing by the signal processing apparatus of modification 2;

FIG. 11 is a block diagram showing the configuration of a signal processing apparatus according to a second embodiment;

FIG. 12 is an explanatory diagram of one aspect of the second embodiment;

FIG. 13 is a diagram showing the overall flow of acoustic signal processing by the signal processing apparatus of the second embodiment;

FIG. 14 is an explanatory diagram of synthesizing adjusted auxiliary acoustic signal in the second embodiment;

FIG. 15 is an explanatory diagram of synthesizing adjusted auxiliary acoustic signal in the second embodiment;

FIG. 16 is an explanatory diagram of synthesizing auxiliary acoustic signal in the second embodiment;

FIG. 17 is a diagram showing an experimental system; and

FIG. 18 is a diagram showing experimental results.

DETAILED DESCRIPTION

Hereinafter, an embodiment of the present invention is described in detail based on the drawings.

Note that, in the drawings for describing the embodiment, the same components are denoted by the same reference sign in principle, and the repetitive description thereof is omitted.

A signal processing apparatus according to one aspect of the present disclosure includes means for receiving an input acoustic signal, means for acquiring a first acoustic signal having a periodic variation corresponding to the frequency of a gamma wave, and means for outputting an output acoustic signal based on the acquired first acoustic signal and a second acoustic signal based on the input acoustic signal.

(1) First Embodiment

A first embodiment will be described.

(1-1) Configuration of Acoustic System

The configuration of the acoustic system will be described. FIG. 1 is a block diagram showing the configuration of the acoustic system of the first embodiment.

As shown in FIG. 1, the acoustic system 1 includes a signal processing apparatus 10, a sound output device 30, and a sound source device 50.

The signal processing apparatus 10 and the sound source device 50 are connected to each other via a predetermined interface capable of transmitting acoustic signals. The interface is, for example, SPDIF (Sony Philips Digital Interface), HDMI (registered trademark) (High-Definition Multimedia Interface), a pin connector (RCA pin), or an audio interface for headphones. The interface may be a wireless interface using Bluetooth (registered trademark) or the like. The signal processing apparatus 10 and the sound output device 30 are similarly connected to each other via a predetermined interface. The acoustic signal in the first embodiment includes either or both of an analog signal and a digital signal.

The signal processing apparatus 10 performs acoustic signal processing on the input acoustic signal acquired from the sound source device 50. Acoustic signal processing by the signal processing apparatus 10 includes at least modulation processing of an acoustic signal (details will be described later). Also, the acoustic signal processing by the signal processing apparatus 10 may include conversion processing (for example, separation, extraction, or synthesis) of acoustic signals. Furthermore, the acoustic signal processing by the signal processing apparatus 10 may further include acoustic signal amplification processing similar to that of an AV amplifier, for example. The signal processing apparatus 10 sends the output acoustic signal generated by the acoustic signal processing to the sound output device 30. The signal processing apparatus 10 is an example of an information processing apparatus.

The sound output device 30 generates sound according to the output acoustic signal acquired from the signal processing apparatus 10. The sound output device 30 may include, for example, a loudspeaker (amplified speaker (powered speaker)).), headphones, or earphones.

The sound output device 30 can also be configured as one device together with the signal processing apparatus 10. Specifically, the signal processing apparatus 10 and the sound output device 30 can be implemented as a TV, radio, music player, AV amplifier, speaker, headphone, earphone, smart phone, or PC. The signal processing apparatus 10 and the sound output device 30 constitute a cognitive function improvement system.

Sound source device 50 sends an input acoustic signal to signal processing apparatus 10. The sound source device 50 is, for example, a TV, a radio, a music player, a smart phone, a PC, an electronic musical instrument, a telephone, a video game console, a game machine, or a device that conveys an acoustic signal by broadcasting or information communication.

(1-1-1) Configuration of Signal Processing Apparatus

A configuration of the signal processing apparatus will be described. FIG. 2 is a block diagram showing the configuration of the signal processing apparatus of the first embodiment.

As shown in FIG. 2, the signal processing apparatus 10 includes a storage device 11, a processor 12, an input/output interface 13, and a communication interface 14. The signal processing apparatus 10 is connected to the display 21.

The memory 11 is configured to store a program and data. The memory 11 is, for example, a combination of a ROM (read only memory), a RAM (random access memory), and a storage (for example, a flash memory or a hard disk). The program and data may be provided via a network, or may be provided by being recorded on a computer-readable recording medium.

Programs include, for example, the following programs:
OS (Operating System) program; and
program of an application that executes an information processing.
The data includes, for example, the following data:
Databases referenced in information processing; and
Data obtained by executing an information processing (that is, an execution result of an information processing).

The processor 12 is a computer that implements the functions of the signal processing apparatus 10 by reading and executing programs stored in the storage device 11. At least part of the functions of the signal processing apparatus 10 may be realized by one or more dedicated circuits. Processor 12 is, for example, at least one of the following:

CPU (Central Processing Unit);
GPU (Graphic Processing Unit);
ASIC (Application Specific Integrated Circuit);
FPGA (Field Programmable Array); and
DSP (digital signal processor).

The input/output interface 13 is configured to acquire user instructions from input devices connected to the signal processing apparatus 10 and to output information to output devices connected to the signal processing apparatus 10.

The input device is, for example, the sound source device 50, physical buttons, keyboard, a pointing device, a touch panel, or a combination thereof.

The output device is, for example, display 21, sound output device 30, or a combination thereof.

Further, the input/output interface 13 may include signal processing hardware such as A/D converters, D/A converters, amplifiers, mixers, filters, and the like.

The communication interface 14 is configured to control communication between the signal processing apparatus 10 and an external device (e.g., the sound output device 30 or the sound source device 50).

The display 21 is configured to display images (still images or moving images). The display 21 is, for example, a liquid crystal display or an organic EL display.

(1-2) One Aspect of the Embodiment

One aspect of the first embodiment will be described. FIG. 3 is an explanatory diagram of one aspect of the first embodiment.

(1-2-1) Outline of the Embodiment

As shown in FIG. 3, the signal processing apparatus 10 acquires an input acoustic signal from the sound source device 50. The signal processing apparatus 10 generates a plurality of intermediate acoustic signals including a first acoustic signal and a second acoustic signal based on the input acoustic signal. In the example of FIG. 3, the first acoustic signal is a partial signal corresponding to the acoustic component of the input acoustic signal whose sound source is a musical instrument, and the second acoustic signal is a partial signal corresponding to the acoustic component of the input acoustic signal whose sound source is vocal.

The signal processing apparatus 10 modulates the first acoustic signal, which is part of the intermediate acoustic signals, to generate a modulated first acoustic signal. Modulation is, for example, amplitude modulation using a modulation function with a frequency between 35 Hz and 45 Hz. As a result, a change in amplitude (strength of volume) corresponding to the frequency is added to the first acoustic signal. The signal processing apparatus 10 does not modulate the second acoustic signal, which is the remainder of the intermediate acoustic signals.

The signal processing apparatus 10 generates an output acoustic signal based on the partially modulated intermediate acoustic signals (that is, the modulated first acoustic signal and the second acoustic signal). The signal processing apparatus 10 sends the output acoustic signal to the sound output device 30. The sound output device 30 generates sound according to the output acoustic signal.

A user US1 (an example of a "listener") listens to sounds emitted from the sound output device 30. The user US1 is, for example, a patient with dementia, a person with pre-dementia, or a healthy person who expects prevention of dementia. As mentioned above, the output acoustic signal is based on the first acoustic signal modulated using a modulation function having a frequency between 35 Hz and 45 Hz. Therefore, when the user US1 listens to the sound emitted from the sound output device 30, gamma waves are induced in the brain of the user US1. As a result, an effect of improving the cognitive function of the user US1 (for example, treating or preventing dementia) can be expected. On the other hand, since the second acoustic signal is not modulated, the deterioration of the acoustic experience of the user US1 with respect to the second acoustic signal is reduced.

(1-2-2) Experimental Results

Experiments conducted to verify the effects of the technique of the present disclosure will be described.

In this experiment, 17 young subjects with normal hearing were made to listen to an output sound based on an acoustic signal generated by the technology of the present disclosure, and the degree of gamma wave induction in the subject's brain at that time was measured. evaluated. For comparison, we also evaluated the degree of gamma wave induction when listening to an output sound based on an acoustic signal generated by a method different from the technique of the present disclosure. The degree of gamma wave induction was measured by electrodes attached to the subject's head. Headphones worn on the subject's head were used as an sound output device that emits an output sound in response to the generated acoustic signal.

FIG. 17 is a diagram showing an experimental system. A sound stimulus (output sound) was presented through headphones to the subject in a quiet magnetically shielded room. An LCD monitor was placed in front of the experimental participants and a short silent animation video was played to keep the subject's level of consciousness constant. Active electrodes for electroencephalogram measurement were placed on the subject's head.

Recorded TV news programs and music programs were prepared as sound stimuli to be presented to the subjects. From the news programs, we selected and used four parts: opening narration, economics, entertainment, and weather forecasts. From the music program, 2 female singer solos, a male singer solo, and a male group were selected and used. These sound sources (unmodulated sounds) were also processed using the techniques of the present disclosure to generate partially modulated acoustic signals (partially modulated sounds). Specifically, the sound source was separated into speech (human voice) and other background sounds using commercially available speech separation software. A partially modulated sound was generated by synthesizing the modulated background sound obtained by amplitude-modulating the background sound using a 40 Hz sine wave as a modulation function and the voice not amplitude-modulated. For comparison, an acoustic signal (fully modulated sound) was also generated by amplitude-modulating the entire sound source before separation with the same modulation function. In addition, a 1 kHz sine wave and a modulated sine wave modulated with a 40 Hz sine wave were generated. Furthermore, a sound consisting of a pulse train with an interval of 40 Hz (one pulse includes one wave of 1 kHz sine wave) was generated. In summary, the sound stimuli used in this experiment were nine patterns of: a pulse train S1, a modulated 1 kHz sine wave S2, an unmodulated 1 kHz sine wave S3, a fully modulated news source S4, a partially modulated news source S5, and an unmodulated news source S6, fully modulated music sound source S7, partially modulated music sound source S8, and unmodulated music sound source S9.

The duration of each sound stimulus was 15 seconds, and each pattern was randomly presented four times. These stimuli were presented by headphones at an equivalent noise level of 72 dB. A PLI (Phase Locking Index) was calculated for each stimulation pattern for electroencephalogram waveforms obtained from active electrodes placed on the subject's Cz while the stimulation was presented.

FIG. 18 is a diagram showing experimental results. Specifically, FIG. 18 shows the average value and standard deviation of the PLI of 17 subjects for nine patterns of sound stimulation from S1 to S9. As shown in FIG. 18, PLI improvement was observed for all modulated sounds (S2, S4, S5, S7 and S8) relative to unmodulated sounds (S3, S6 and S9). All PLIs of unmodulated sounds were less than 0.03. The PLI of the partially modulated sounds (S5 and S8) generated using the techniques of this disclosure is less than the PLI of the fully modulated sounds (S2, S4, and S7), but is significantly larger than the PLI of the unmodulated sounds (S3, S6, and S9). In addition, while the voice part (voice reading the news or singing voice) is modulated in the fully modulated sound, the voice part of the partially modulated sound is not modulated and the clarity of the voice is not impaired. Thus, the partially modulated sound is less degraded in the acoustic experience for the listener than a fully modulated sound. That is, according to this experiment, it was shown that the user's gamma waves can be induced while suppressing the deterioration of the acoustic experience by using the technology of the present disclosure. This result indicates the possibility that the acoustic system can improve the user's cognitive function by outputting sound stimuli that the user does not feel uncomfortable even if they listen to it on a daily basis.

(1-3) Acoustic Signal Processing

Acoustic signal processing according to the first embodiment will be described. FIG. 4 is a diagram showing the overall flow of acoustic signal processing by the signal processing apparatus of the first embodiment. The processing in FIG. 4 is implemented by the processor 12 of the signal processing apparatus 10 reading and executing the program stored in the storage device 11. At least part of the processing in FIG. 4 may be realized by one or more dedicated circuits. The same applies to the processing in FIGS. 9 and 10, which will be described later. FIG. 5 is an explanatory diagram of the frequency characteristics of an acoustic signal. FIG. 6 is an illustration of the temporal characteristics of an acoustic signal. FIG. 7 is an explanatory diagram of characteristics of the output of the acoustic signal.

The acoustic signal processing in FIG. 4 is started when any of the following start conditions is satisfied.

The acoustic signal processing of FIG. 4 was called by another process or an instruction from the outside.

The user performed an operation to call the acoustic signal processing in FIG. 4.

The signal processing apparatus 10 has entered a predetermined state (for example, the power has been turned on).

The specified date and time has arrived.

A predetermined time has passed since a predetermined event (for example, activation of the signal processing apparatus 10 or previous execution of the acoustic signal processing in FIG. 4).

As shown in FIG. 4, the signal processing apparatus 10 executes acquisition of an input acoustic signal (S110).

Specifically, the signal processing apparatus 10 receives an input acoustic signal sent from the sound source device 50.

In step S110, the signal processing apparatus 10 may further perform A/D conversion of the input acoustic signal.

The input acoustic signal corresponds, for example, to at least one of the following:

Musical content (e.g., singing, playing, or a combination thereof (i.e., a piece of music). It may include audio content that accompanies the video content.);

Audio content (for example, reading, narration, announcement, broadcast play, solo performance, conversation, monologue, or a combination thereof, etc. It may include audio content accompanying video content); and Other acoustic content (e.g., electronic, ambient, or mechanical sounds).

However, singing or voice content is not limited to sounds produced by human vocal organs, but may include sounds generated by speech synthesis technology.

After step S110, the signal processing apparatus 10 executes generation of an intermediate acoustic signal (S111).

Specifically, the signal processing apparatus 10 generates an intermediate acoustic signal including a plurality of acoustic signals based on the input acoustic signal acquired in step S110.

The intermediate acoustic signal may have three or more acoustic signals, not limited to two, but the following description assumes that the intermediate acoustic signal has the first acoustic signal and the second acoustic signal. The first acoustic signal and the second acoustic signal differ in at least one characteristic. For example, one of the first acoustic signal and the second acoustic signal has a predetermined characteristic, and the other does not have the characteristic. Alternatively, one of the first acoustic signal and the second acoustic signal is qualitatively or quantitatively superior in a predetermined characteristic, and the other is qualitatively or quantitatively inferior in the characteristic. A characteristic may be determined based on an input operation by a user or another person, or an instruction from the outside, or may be determined by an algorithm. For example, the signal processing apparatus 10 may determine characteristics for generating the intermediate acoustic signal based on the result of analyzing the input acoustic signal.

In the following description, the other person is, for example, at least one of the following:

User's family, friends, or acquaintances;

Medical personnel (for example, the user's doctor);

Creator or provider of content corresponding to the input acoustic signal;

Provider of the signal processing apparatus 10; and

Administrators of facilities used by users.

The characteristic may be, for example, at least one of the following:

Characteristics of sounds (especially qualitative characteristics);

Frequency characteristics;

Characteristics of time;

Characteristics of amplitude; and

Characteristics of output.

A sound characteristic is, for example, an acoustic component that satisfies one or more sound qualitative conditions. The sound qualitative condition may be, for example, a condition relating to at least one of the following:

Type of sound source (e.g., object, instrument, vocal, music, speech, or input channel);

Direction of arrival of sound; and

Effect of improving cognitive function or preventing dementia.

In the example of FIG. 3, the first acoustic signal includes acoustic components whose sound sources are musical instruments, and the second acoustic signal includes acoustic components whose sound sources are vocals.

A frequency characteristic is, for example, an acoustic component that satisfies one or more frequency conditions. Specifically, as shown in FIG. 5, the first acoustic signal does not include acoustic components in a specific frequency band f1-f2, and the second acoustic signal includes acoustic components in the frequency band f1-f2. A particular frequency band may be defined, for example, based on the frequency band of human voice.

A temporal characteristic is, for example, an acoustic component that satisfies one or more temporal conditions. Specifically, as shown in FIG. 6, the first acoustic signal does not comprise acoustic components in a particular time period t1-t2, and the second acoustic signal comprises such acoustic components. When sound components in a plurality of time periods are defined as temporal characteristics, each time period may be set periodically or may be set aperiodically.

Amplitude characteristics are, for example, acoustic components that satisfy one or more amplitude conditions. As an example, the amplitude characteristic is that the change in volume over time conforms to a predetermined pattern.

Output characteristics are, for example, sounds (acoustic components) that a listener perceives as coming from a sound source in a given direction or position. Specifically, the output characteristic is, for example, an acoustic component that satisfies one or more output conditions.

As a first example, the output condition is that the sound output device 30 is associated with a speaker in a specific direction that constitutes a surround system (that is, output from a specific speaker in the end). In the example of FIG. 7, the sound output device 30 corresponds to a surround speaker system including speakers 30-1 to 30-4. A first acoustic signal is associated with a speaker 30-3, 30-4 in a particular direction (i.e., output from the rear left or rear right), and a second acoustic signal is not associated with the speaker 30-3, 30-4 in question. (instead, associated with speakers 30-1, 30-2 (i.e., output from front left or front right)).

As a second example, the output condition is that the acoustic signal is associated with a virtual sound source set at a particular direction or position in the object audio.

If the input acoustic signal acquired in step S110 is preliminarily separated into an acoustic signal having a predetermined characteristic and an acoustic signal not having the characteristic (for example, if the input acoustic signal corresponds to a multi-channel acoustic signal associated each speaker constituting a surround system as the sound output device 30, step S111 can be omitted. In this case, the input acoustic signal is treated as an intermediate acoustic signal. On the other hand, if the input acoustic signal has not been pre-separated into an acoustic signal with a predetermined characteristic and an acoustic signal without the characteristic, the signal processing apparatus 10 converts the input acoustic signal into an intermediate acoustic signal. For example, the signal processing apparatus 10 extracts or separates an acoustic signal having predetermined characteristics from the input acoustic signal.

After step S111, the signal processing apparatus 10 executes selection of a target signal (S112). Specifically, the signal processing apparatus 10 selects a part of the plurality of acoustic signals (for example, the first acoustic signal) included in the intermediate acoustic signal generated in step S111 as the target signal. Which acoustic signal to select as the target signal may be determined based on an input operation by the user or other person, or an instruction from the outside, or may be determined by an algorithm. For example, the signal processing apparatus 10 may determine the target signal based on the characteristics of the acoustic signal included in the intermediate acoustic signal (balance between voice and music, volume change, type of music, timbre, or other characteristics). Thereby, the signal processing apparatus 10 can select the target signal so that the improvement effect of the cognitive function by modulation becomes higher, or select the target signal so as to make the user less uncomfortable.

After step S112, the signal processing apparatus 10 executes modulation of the target signal (S113). Specifically, the signal processing apparatus 10 modulates the target signal selected in step S112. As an example, the signal processing apparatus 10 amplitude-modulates the target signal using a modulation function having a frequency corresponding to a gamma wave (for example, a frequency between 35 Hz and 45 Hz). Specifically, let A(t) be a modulation function having a periodicity between 35 Hz and 45 Hz, let X(t) be a function representing the waveform of the first acoustic signal before modulation, and let Y(t) be the function representing the waveform of the modulated first acoustic signal, $$Y(t)=A(t) \times X(t)$$

holds. As a result, a change in amplitude corresponding to the frequency is added to the target signal.

After step S113, the signal processing apparatus 10 executes generation of an output acoustic signal (S114).

Specifically, the signal processing apparatus 10 generates an output acoustic signal based on the acoustic signal (hereinafter referred to as "non-target signal") that was not selected as the target signal in step S112 from among the intermediate acoustic signals, and the target signal modulated in step S113.

When the non-target signal and the modulated target signal match the output format of the sound output device 30 (for example, the non-target signal and the modulated target signal correspond to multi-channel acoustic signals associated with each speaker that constitutes the surround system as the sound output device 30), step S114 can be omitted. In this case, the non-target signal and the modulated target signal are treated as output acoustic signals.

On the other hand, if the non-target signal and the modulated target signal do not match the output format of the sound output device 30, the signal processing apparatus 10 converts the non-target signal and the modulated target signal into an output acoustic signal. Specifically, the signal processing apparatus 10 synthesizes two or more acoustic signals of the non-target signal and the modulated target signal, or extracts or separates the acoustic signal from at least one of the non-target signal and the modulated target signal. Although the method of synthesizing the acoustic signal is not limited, for example, signal summation processing, HRTF (Head Related Transfer Function) convolution processing, transfer function convolution processing that provides position information of the sound source, or summation processing after these convolution processing may be included. In step S114, the signal processing apparatus 10 may further perform at least one of amplification, volume control, and D/A conversion of the output acoustic signal.

After step S114, the signal processing apparatus 10 executes transmission of an output acoustic signal (S115).

Specifically, the signal processing apparatus 10 sends the output acoustic signal generated in step S114 to the sound output device 30. The sound output device 30 generates sound according to the output acoustic signal.

The signal processing apparatus 10 ends the acoustic signal processing in FIG. 4 at step S115.

Note that the signal processing apparatus 10 may collectively perform the processing in FIG. 4 for an input acoustic signal having a certain reproduction period (for example, one piece of music content), or may repeat the processing in FIG. 4 for each predetermined reproduction period of the input acoustic signal (for example, every 100 ms). Alternatively, the signal processing apparatus 10 may continuously perform modulation processing on an input acoustic signal, such as modulation by analog signal processing, and output a modulated acoustic signal. The processing shown in FIG. 4 may be ended according to a specific termination condition (for example, the passage of a certain period of time, the user's operation, or the output history of the modulated sound reaching a predetermined state).

(1-4) Summary

As described above, the signal processing apparatus 10 according to the first embodiment generates a modulated first acoustic signal having a change in amplitude corresponding to the frequency of the gamma wave by amplitude-modulating the first acoustic signal having predetermined characteristics among the input acoustic signal. The signal processing apparatus 10 outputs an output acoustic signal based on the modulated first acoustic signal and the second acoustic signal of the input acoustic signal that does not have the predetermined characteristic. As a result, the amplitude of the first acoustic signal can be increased or decreased in a predetermined cycle while suppressing deterioration of the acoustic experience of the second acoustic signal. Furthermore, the sound output device 30 may make the user (for example, a dementia patient, a person with pre-dementia, or a healthy person who expects to prevent dementia) listen to a sound according to such an output acoustic signal. This induces gamma waves in the user's brain due to variations in the amplitude of the first acoustic signal. As a result, the effect of improving the user's cognitive function (for example, treating or preventing dementia) can be expected.

The first acoustic signal may be an acoustic signal including a sound (acoustic component) of a predetermined sound source type in the input acoustic signal. As a result, it is possible to increase or decrease the amplitude of the first acoustic signal in a predetermined cycle while suppressing deterioration of the acoustic experience other than the sound of the predetermined sound source type.

The first acoustic signal may be an acoustic signal comprising a sound (acoustic component) that a listener perceives as coming from a sound source in a predetermined direction, among the input acoustic signals. As a result, it is possible to increase or decrease the amplitude of the first acoustic signal at a predetermined cycle while suppressing the deterioration of the sound experience other than the sound coming from the sound source in the predetermined direction (perceived by the listener).

The first acoustic signal may be an acoustic signal including sounds (acoustic components) in a predetermined frequency band among the input acoustic signals. As a result, it is possible to increase or decrease the amplitude of the first acoustic signal in a predetermined cycle while suppressing deterioration of the sound experience other than sounds in a predetermined frequency band.

The first acoustic signal may be an acoustic signal including a sound (acoustic component) of a predetermined time period in the input acoustic signal. As a result, the amplitude of the first acoustic signal can be increased or decreased in a predetermined cycle while suppressing the deterioration of the sound experience other than the sound in the predetermined time period.

The second acoustic signal may be an acoustic signal obtained by separating the first acoustic signal from the input acoustic signal. As a result, since the acoustic component included in the input acoustic signal is included in either the first acoustic signal or the second acoustic signal, it is possible to suppress the deterioration of the acoustic experience due to the disappearance of the acoustic component.

The output acoustic signal may have amplitude variations corresponding to frequencies between 35 Hz and 45 Hz. As a result, when the user hears the sound corresponding to the output acoustic signal, it can be expected that gamma waves will be induced in the user's brain.

The input acoustic signal may be an audio signal corresponding to music content. As a result, the motivation of the user to listen to the sound corresponding to the output acoustic signal can be improved.

(1-5) Modification

A modification of the first embodiment will be described.

(1-5-1) Modification 1

Modification 1 is described. Modification 1 is an example in which a first acoustic signal among input acoustic signals is modulated with a first modulation degree, and a second acoustic signal is modulated with a second modulation degree different from the first modulation degree.

(1-5-1-1) One Aspect of Modification 1

An aspect of Modification 1 will be described. FIG. 8 is an explanatory diagram of one aspect of Modification 1.

As shown in FIG. 8, the signal processing apparatus 10 acquires an input acoustic signal from the sound source device 50. The signal processing apparatus 10 generates a plurality of intermediate acoustic signals including a first acoustic signal and a second acoustic signal based on the input acoustic signal. In the example of FIG. 8, the first acoustic signal corresponds to the acoustic component of the input acoustic signal whose sound source is a musical instrument, and the second acoustic signal corresponds to the acoustic component of the input acoustic signal whose sound source is vocal.

The signal processing apparatus 10 modulates the first acoustic signal and the second acoustic signal included in the intermediate acoustic signals to generate the modulated first acoustic signal and the modulated second acoustic signal. Modulation is, for example, amplitude modulation using a modulation function with a frequency between 35 Hz and 45 Hz. As a result, a change in amplitude corresponding to the frequency is added to the acoustic signal.

Note that the signal processing apparatus 10 uses different degrees of modulation for the first acoustic signal and the second acoustic signal. As an example, the signal processing apparatus 10 modulates the first acoustic signal with a first degree of modulation, and modulates the second acoustic signal with a second degree of modulation that is smaller than the first degree of modulation. That is, the modulated first acoustic signal has a relatively intense change in amplitude (strength of volume) corresponding to the frequency of the modulation function, and the modulated second acoustic signal has a relatively gentle change in amplitude corresponding to the frequency. (the deviation from the original sound is small).

The signal processing apparatus 10 generates an output acoustic signal based on the intermediate acoustic signals (that is, the modulated first acoustic signal and the modulated second acoustic signal) thus partially modulated with different degrees of modulation. The signal processing apparatus 10 sends the output acoustic signal to the sound output device 30. The sound output device 30 generates sound according to the output acoustic signal.

A user US1 listens to the sound emitted from the sound output device 30. As mentioned above, the output acoustic signal is based on the first and second acoustic signals modulated using a modulation function having a frequency between 35 Hz and 45 Hz. Therefore, when the user US1 listens to the sound emitted from the sound output device 30, gamma waves are induced in the brain of the user US1. As a result, the effect of improving the cognitive function of the user US1 (for example, treating or preventing dementia) can be expected. On the other hand, since the second acoustic signal is modulated with a relatively small second modulation degree, deterioration of the acoustic experience of the user US1 with respect to the second acoustic signal is suppressed.

(1-5-1-2) Acoustic Signal Processing

Acoustic signal processing of modification 1 will be described. FIG. 9 is a diagram showing an overall flow of acoustic signal processing by the signal processing apparatus of Modification 1.

The acoustic signal processing in FIG. 9 is started when any of the following start conditions is satisfied.

The acoustic signal processing of FIG. 9 was called by another process or an instruction from the outside.

The user performed an operation to call the acoustic signal processing in FIG. 9.

The signal processing apparatus 10 has entered a predetermined state (for example, the power has been turned on).

The specified date and time has arrived.

A predetermined time has passed since a predetermined event (for example, activation of the signal processing apparatus 10 or previous execution of the acoustic signal processing in FIG. 9).

As shown in FIG. 9, the signal processing apparatus 10 executes acquisition of the input acoustic signal (S110) and generation of the intermediate acoustic signal (S111), as in FIG. 4.

After step S111, the signal processing apparatus 10 executes selection of a target signal (S212). Specifically, the signal processing apparatus 10 selects a part of the plurality of acoustic signals (for example, the first acoustic signal) included in the intermediate acoustic signal generated in step S111 as the first target signal. Further, the signal processing apparatus 10 selects a part of the plurality of acoustic signals (e.g., second acoustic signal) included in the intermediate acoustic signal generated in step S111 as the second target signal. Which acoustic signal is selected as the first target signal or the second target signal may be determined based on an input operation by the user or other person, or an instruction from the outside, or may be determined by an algorithm. For example, the signal processing apparatus 10 may determine the first and second target signals based on the characteristics of the plurality of acoustic signals in the intermediate acoustic signal (balance between voice and music, volume change, type of music, timbre, or other characteristics). As a result, the signal processing apparatus 10 can select the first target signal and the second target signal so that the effect of improving cognitive function by modulation is higher, or select the first target signal and the second target signal so that the user feels less uncomfortable.

The first target signal and the second target signal may be acoustic signals with different characteristics. Alternatively, one of the first target signal and the second target signal may be an acoustic signal having a predetermined characteristic, and the other may be an acoustic signal not having the characteristic.

After step S212, the signal processing apparatus 10 executes modulation of the target signal (S213). Specifically, the signal processing apparatus 10 modulates the first target signal and the second target signal selected in step S212 with different degrees of modulation. As an example, the signal processing apparatus 10 performs amplitude modulation on the first target signal and the second target signal using a modulation function having a frequency corresponding to a gamma wave (for example, a frequency between 35 Hz and 45 Hz) with the different degrees of modulation. Thereby, a change in amplitude corresponding to the frequency is added to the first target signal and the second target signal.

The first degree of modulation or the second degree of modulation may be determined based on an input operation by a user or other person, or an instruction from the outside, or may be determined by an algorithm. For example, the signal processing apparatus 10 may determine the first and second degrees of modulation based on characteristics of the first and second acoustic signals (balance between voice and music, volume change, type of music, timbre, or other characteristics). Thereby, the signal processing apparatus 10 can determine the first modulation degree and the second modulation degree so that the improvement effect of the cognitive function by modulation becomes higher, or determine the first modulation degree and the second modulation degree so that the user feels less uncomfortable.

After step S213, the signal processing apparatus 10 executes generation of an output acoustic signal (S214).

Specifically, the signal processing apparatus 10 generates an output acoustic signal based on the first target signal and the second target signal modulated in step S213.

When the modulated first target signal and the modulated second target signal match the output format of the sound output device 30 (for example, when the modulated first target signal and the modulated second target signal are associated with each speaker constituting the surround system as the sound output device 30), step S214 can be omitted. In this case, the modulated first target signal and the modulated second target signal are treated as output acoustic signals. On the other hand, when the modulated first target signal and the modulated second target signal do not match the output format of the sound output device 30, the signal processing apparatus 10 converts the modulated first target signal and the modulated second target signal into output acoustic signal. For example, the signal processing apparatus 10 synthesizes two or more acoustic signals of the modulated first target signal and the modulated second target signal, or extracts or separates an acoustic signal from at least one of the modulated first target signal and the modulated second target signal.

In step S214, the signal processing apparatus 10 may further perform at least one of amplification and D/A conversion of the output acoustic signal.

However, if there is an acoustic signal that was not selected as the target signal in step S212 (hereinafter referred to as "non-target signal") among the intermediate acoustic signals, the signal processing apparatus 10 may generate the output acoustic signal based on the modulated first target signal, the modulated second target signal and the non-target signal.

After step S214, the signal processing apparatus 10 executes transmission of the output acoustic signal (S115), as in FIG. 4.

The signal processing apparatus 10 ends the acoustic signal processing in FIG. 9 at step S115.

(1-5-1-3) Summary

As described above, the signal processing apparatus 10 of Modification 1 amplitude-modulates the first acoustic signal among the intermediate acoustic signals based on the input acoustic signal at the first modulation degree, and amplitude-modulates the second acoustic signal among the intermediate acoustic signals at the second modulation degree different from the first modulation degree. Thereby, the amplitude of both the first acoustic signal and the second acoustic signal can be increased or decreased in a predetermined cycle while suppressing the deterioration of the acoustic experience regarding the acoustic signal amplitude-modulated with a relatively small degree of modulation. Furthermore, the sound output device 30 may make the user (for example, a dementia patient, a person with pre-dementia, or a healthy person who expects to prevent dementia) listen to a sound according to such an output acoustic signal. This induces gamma waves in the user's brain due to variations in the amplitudes of the first and second acoustic signals. As a result, the effect of improving the user's cognitive function (for example, treating or preventing dementia) can be expected.

Note that the signal processing apparatus 10 amplitude-modulates the first acoustic signal with the first modulation function, and amplitude-modulates the second acoustic signal with the second modulation function different from the first modulation function, by the same processing as described above. may In this case as well, the same effect as in the case of using the first modulation degree and the second modulation degree can be expected.

(1-5-2) Modification 2

Modification 2 is described. Modification 2 is an example in which each acoustic signal included in the intermediate acoustic signal is modulated with an individual degree of modulation.

(1-5-2-1) Acoustic Signal Processing

Acoustic signal processing of modification 2 will be described. FIG. 10 is a diagram showing the overall flow of acoustic signal processing by the signal processing apparatus of Modification 2.

The acoustic signal processing in FIG. 10 is started when any of the following start conditions is satisfied.

The acoustic signal processing of FIG. 10 was called by another process or an instruction from the outside.

The user performed an operation for calling the acoustic signal processing in FIG. 10.

The signal processing apparatus 10 has entered a predetermined state (for example, the power has been turned on).

The specified date and time has arrived.

A predetermined time has passed since a predetermined event (for example, activation of the signal processing apparatus 10 or previous execution of the acoustic signal processing in FIG. 10).

As shown in FIG. 10, the signal processing apparatus 10 executes the acquisition of the input acoustic signal (S110) and generation of the intermediate acoustic signal (S111), as in FIG. 4.

After step S111, the signal processing apparatus 10 executes assignment of degree of modulation (S312).

Specifically, the signal processing apparatus 10 individually assigns modulation degrees to each of the plurality of acoustic signals included in the intermediate acoustic signal generated in step S111.

The degree of modulation assigned to each acoustic signal is different. Any acoustic signal may be assigned a degree of modulation of '0'. That is, any acoustic signal included in the intermediate acoustic signal may not be modulated.

The degree of modulation assigned to each acoustic signal may be determined based on an input operation by a user or other person, or an instruction from the outside, or may be determined by an algorithm. For example, the signal processing apparatus 10 determines each degree of modulation based on the characteristics of a plurality of acoustic signals included in the intermediate acoustic signal (balance between voice and music, volume change, type of music, timbre, or other characteristics). Thereby, the signal processing apparatus 10 can determine the degree of modulation such that the effect of improving the cognitive function by modulation becomes higher, or the degree of modulation becomes less uncomfortable for the user.

After step S312, the signal processing apparatus 10 executes modulation of the intermediate acoustic signal (S313).

Specifically, the signal processing apparatus 10 modulates each acoustic signal included in the intermediate acoustic signal with the degree of modulation assigned in step S312. As an example, the signal processing apparatus 10 performs amplitude modulation using a modulation function having a frequency corresponding to a gamma wave (for example, a frequency between 35 Hz and 45 Hz) for each acoustic signal with an individually assigned modulation degree. As a result, amplitude changes corresponding to the frequencies are added to each acoustic signal.

After step S313, the signal processing apparatus 10 executes generation of an output acoustic signal (S314).

Specifically, the signal processing apparatus 10 generates an output acoustic signal based on the intermediate acoustic signal modulated in step S313.

When the modulated intermediate acoustic signal matches the output format of the sound output device 30 (for example, when the modulated intermediate acoustic signal corresponds to a multi-channel acoustic signal associated with each speaker that constitutes the surround system as the sound output device 30), step S314 can be omitted. In this case, the modulated intermediate acoustic signal is treated as the output acoustic signal. On the other hand, if the modulated intermediate acoustic signal does not match the output format of the sound output device 30, the signal processing apparatus 10 converts the modulated intermediate acoustic signal into an output acoustic signal. For example, the signal processing apparatus 10 synthesizes two or more of a plurality of acoustic signals included in the intermediate acoustic signal, or extracts or separates an acoustic signal from at least one acoustic signal included in the modulated intermediate acoustic signal.

In step S314, the signal processing apparatus 10 may further perform at least one of amplification and D/A conversion of the output acoustic signal.

After step S314, the signal processing apparatus 10 executes transmission of the output acoustic signal (S115), as in FIG. 4. The signal processing apparatus 10 ends the acoustic signal processing of FIG. 10 at step S115.

(1-5-2-2) Summary

As described above, the signal processing apparatus 10 of Modification 2 amplitude-modulates each acoustic signal included in the intermediate acoustic signal based on the input acoustic signal with the individually assigned degree of modulation. This makes it possible to increase or decrease the amplitude of an acoustic signal to which a non-zero degree of modulation is assigned in a predetermined cycle while suppressing the deterioration of the acoustic experience of the acoustic signal amplitude-modulated with a relatively small degree of modulation. Furthermore, the sound output device 30 may make the user (for example, a dementia patient, a person with pre-dementia, or a healthy person who expects to prevent dementia) listen to a sound according to such an output acoustic signal. This induces gamma waves in the user's brain due to variations in the amplitude of the acoustic signal assigned a non-zero degree of modulation. As a result, the effect of improving the user's cognitive function (for example, treating or preventing dementia) can be expected.

Note that the signal processing apparatus 10 may modulate each acoustic signal included in the intermediate acoustic signal with an individually assigned modulation function by performing the same processing as described above. In this case as well, the same effects as in the case of using individually assigned degrees of modulation can be expected.

(2) Second Embodiment

A second embodiment will be described.

(2-1) Configuration of Acoustic System

The configuration of the acoustic system will be described. The configuration of the acoustic system of the second embodiment is similar to that of the acoustic system of the first embodiment shown in FIG. 1.

(2-1-1) Configuration of Signal Processing Apparatus

A configuration of the signal processing apparatus will be described. FIG. 11 is a block diagram showing the configuration of the signal processing apparatus of the second embodiment.

As shown in FIG. 11, the signal processing apparatus 10 includes a storage device 11, a processor 12, an input/output interface 13, and a communication interface 14. The signal processing apparatus 10 is connected to a display 21 and a signal generator 22.

The storage device 11, processor 12, input/output interface 13, communication interface 14, and display 21 are similar to those in the first embodiment.

The signal generator 22 generates an acoustic signal (hereinafter referred to as "auxiliary acoustic signal") having periodic variations corresponding to the frequency of the gamma wave. The auxiliary acoustic signal is, for example, a signal having pulses with an interval corresponding to the frequency of gamma waves, but is not limited to this. For example, the auxiliary acoustic signal may be a sine wave corresponding to the gamma wave frequency, or may be generated by applying amplitude modulation to any acoustic signal, such as noise or music. according to the gamma wave frequency. The auxiliary acoustic signal is preferably predetermined such that the component corresponding to the gamma wave frequency is greater than the reference, or adjusted so that the component is greater than the reference. The reference may be determined based on the component of the auxiliary acoustic signal that does not correspond to the gamma wave frequency, or may be determined based on the component of the input acoustic signal that corresponds to the gamma wave frequency. When the input acoustic signal is used as the reference, the auxiliary acoustic signal is a signal containing more components corresponding to the gamma wave frequency than the input acoustic signal. To generate the auxiliary acoustic signal, the modulation described in the first embodiment or its modifications may be performed, or other modulations may be performed. Signal generator 22 is an example of an input device. Note that the function of the signal generator 22 may be implemented by the processor 12. In this case, the signal processing apparatus 10 does not have to be connected to the signal generator 22.

(2-2) One Aspect of the Embodiment

One aspect of the second embodiment will be described. FIG. 12 is an explanatory diagram of one aspect of the second embodiment.

As shown in FIG. 12, the signal processing apparatus 10 acquires an input acoustic signal from the sound source device 50. The signal processing apparatus 10 acquires an auxiliary acoustic signal. The signal processing apparatus 10 adjusts the auxiliary acoustic signal based on the input acoustic signal. However, the adjustment may be omitted, and in this case, the "adjusted auxiliary acoustic signal" should be replaced with the "auxiliary acoustic signal" in the following description. The signal processing apparatus 10 generates a synthesized acoustic signal by combining (adding) the adjusted auxiliary acoustic signal to the input acoustic signal.

Here, the adjusted auxiliary acoustic signal has an amplitude change (volume strength) corresponding to a frequency of, for example, between 35 Hz and 45 Hz. Therefore, in the process of generating the synthesized acoustic signal, the periodic variations corresponding to the gamma wave frequency in the input acoustic signal will be reinforced.

The signal processing apparatus 10 generates an output acoustic signal based on the synthesized acoustic signal in which the periodic variation corresponding to the frequency of the gamma wave is enhanced in this way. In the example of FIG. 12, the signal processing apparatus 10 generates a stereo output acoustic signal based on the synthesized acoustic signal. The signal processing apparatus 10 sends the output acoustic signal to the sound output device 30. The sound output device 30 generates sound according to the output acoustic signal. The output acoustic signal output by the signal processing apparatus 10 may be a signal of one channel or a signal of three or more channels depending on the configuration of the sound output device 30.

A user US1 listens to the sound emitted from the sound output device 30. The user US1 is, for example, a patient with dementia, a person with pre-dementia, or a healthy person who expects prevention of dementia. As previously mentioned, the output acoustic signal is based on a synthesized acoustic signal enhanced with periodic variations corresponding to the gamma wave frequency. Therefore, when the user US1 listens to the sound emitted from the sound output device 30, gamma waves are induced in the brain of the user US1. As a result, an effect of improving the cognitive function of the user US1 (for example, treating or preventing dementia) can be expected. On the other hand, since the synthesized acoustic signal contains the unmodulated components of the input acoustic signal, the deterioration of the user US1's audio experience with respect to the input acoustic signal is suppressed.

(2-3) Acoustic Signal Processing

Acoustic signal processing according to the second embodiment will be described. FIG. 13 is a diagram showing the overall flow of acoustic signal processing by the signal processing apparatus of the second embodiment. The processing of FIG. 13 is implemented by the processor 12 of the signal processing apparatus 10 reading and executing the program stored in the storage device 11. At least part of the processing in FIG. 13 may be realized by one or more dedicated circuits. FIG. 14 is an explanatory diagram of synthesis of the adjusted auxiliary acoustic signal in the second embodiment. FIG. 15 is an explanatory diagram of synthesis of the adjusted auxiliary acoustic signal in the second embodiment. FIG. 16 is an explanatory diagram of synthesis of the auxiliary acoustic signal in the second embodiment.

The acoustic signal processing of the second embodiment can be started in response to establishment of a start condition similar to that of the acoustic signal processing of the first embodiment.

As shown in FIG. 13, the signal processing apparatus 10 executes acquisition of the input acoustic signal (S110) as in the first embodiment.

After step S110, the signal processing apparatus 10 acquisition of an auxiliary acoustic signal (S411). Specifically, the signal processing apparatus 10 acquires the auxiliary acoustic signal generated by the signal generator 22.

After step S411, the signal processing apparatus 10 performs adjustment of the auxiliary acoustic signal (S412).

Specifically, the signal processing apparatus 10 adjusts the auxiliary acoustic signal based on the input acoustic signal acquired in step S110.

As a first example of the adjustment of the auxiliary acoustic signal (S412), the signal processing apparatus 10 adjusts the auxiliary acoustic signal so that the amplitude of the periodic variation (e.g., pulse component) corresponding to the frequency of gamma waves in the auxiliary acoustic signal follows the amplitude change of the input acoustic signal, thereby obtaining the adjusted auxiliary acoustic signal. The signal processing apparatus 10 may adjust the auxiliary acoustic signal so as to follow the instantaneous value of the input acoustic signal, or adjust the auxiliary acoustic signal so as to follow the average value of the input acoustic signal in a time window of a predetermined width. As an example, the signal processing apparatus 10 determines the amount of adjustment of the auxiliary acoustic signal amplitude adjustment so that the SN ratio (Signal-Noise Ratio) is constant when the input acoustic signal and the adjusted auxiliary acoustic signal are signal (S) and noise (N), respectively. According to the first example of the adjustment of the auxiliary acoustic signal (S412), as shown in FIG. 14, the user can hear the sound in which the periodic variation corresponding to the gamma wave frequency is enhanced. In this example, the magnitude of the amplitude of the periodic variation corresponding to the frequency of the gamma wave contained in the adjusted auxiliary acoustic signal changes so as to follow the amplitude change of the input acoustic signal. Therefore, fluctuations in how the auxiliary acoustic signal is heard (degree of prominence with respect to the input acoustic signal) when the volume of the input acoustic signal changes are suppressed, and deterioration of the user's sound experience is suppressed. Moreover, even if the volume of the input acoustic signal changes, the user can continuously receive the sound stimulation corresponding to the gamma wave frequency.

As a second example of the adjustment of the auxiliary acoustic signal (S412), the signal processing apparatus 10 adjusts the auxiliary acoustic signal so that the amplitude of the periodic variation (for example, pulse component) corresponding to the frequency of the gamma wave in the auxiliary acoustic signal changes in the opposite direction to the amplitude change of the input acoustic signal, thereby to obtain the adjusted auxiliary acoustic signal. For example, the signal processing apparatus 10 adjusts the auxiliary acoustic signal so as to follow an index that increases as the signal value of the input acoustic signal decreases. For example, such an index may be the reciprocal of the instantaneous value of the input acoustic signal, or may be a value obtained by subtracting the instantaneous value from a fixed value. Alternatively, such an index may be the reciprocal of the average value of the input acoustic signal in a time window of a predetermined width, or may be a value obtained by subtracting the average value from a fixed value. According to the second example of the adjustment of the auxiliary acoustic signal (S412), as shown in FIG. 15, the user can hear the sound in which the periodic fluctuation corresponding to the gamma wave frequency is enhanced. In this example, since the magnitude of the periodic variation corresponding to the frequency of the gamma wave contained in the adjusted auxiliary acoustic signal changes in the opposite direction to the amplitude change of the input acoustic signal, the periodic fluctuation increases in the silent period etc. of the input acoustic signal, while the periodic fluctuation is suppressed in other periods. Therefore, the periodical variation corresponding to the frequency of the gamma wave is strengthened in the period that does not interfere with listening to the sound based on the input acoustic signal, thereby suppressing the deterioration of the user's audio experience.

Note that this step can be omitted, and in this case, "adjusted auxiliary acoustic signal" should be replaced with "auxiliary acoustic signal" in the following description. Even if the adjustment of the auxiliary acoustic signal (S412) is omitted, the user can hear the sound in which the periodic variation corresponding to the gamma wave frequency is enhanced, as shown in FIG. 16. By omitting the adjustment of the auxiliary acoustic signal (S412), the amount of calculation of the signal processing apparatus 10 can be reduced.

After step S412, synthesis of acoustic signals (S413) is executed.

Specifically, the signal processing apparatus 10 generates a synthesized acoustic signal by synthesizing the input acoustic signal obtained in step S110 with the adjusted auxiliary acoustic signal obtained in step S412.

After step S413, the signal processing apparatus 10 executes generation of an output acoustic signal (S414).

Specifically, the signal processing apparatus 10 generates the output acoustic signal based on the synthesized acoustic signal generated in step S413.

When the synthesized acoustic signal matches the output format of the sound output device 30 (for example, when the synthesized acoustic signal corresponds to a multi-channel acoustic signal associated with each speaker constituting the surround system as the sound output device 30), Step S414 can be omitted. In this case, the synthesized acoustic signal is treated as the output acoustic signal.

On the other hand, when the synthesized acoustic signal does not match the output format of the sound output device 30, the signal processing apparatus 10 converts the synthesized acoustic signal into an output acoustic signal. Specifically, the signal processing apparatus 10 synthesizes two or more acoustic signals out of the synthesized acoustic signals, or extracts or separates the acoustic signal from at least one of the synthesized acoustic signals. Although the method of synthesizing the acoustic signal is not limited, for example, signal summation processing, HRTF (Head Related Transfer Function) convolution processing, transfer function convolution processing that provides position information of the sound source, or summation processing after these convolution processing are performed may be included.

In step S414, the signal processing apparatus 10 may further perform at least one of amplification, volume control, and D/A conversion of the output acoustic signal.

After step S414, the signal processing apparatus 10 executes transmission of the output acoustic signal (S115).

Specifically, the signal processing apparatus 10 sends the output acoustic signal generated in step S414 to the sound output device 30. The sound output device 30 generates sound according to the output acoustic signal.

The signal processing apparatus 10 ends the acoustic signal processing of FIG. 13 at step S115.

Note that the signal processing apparatus 10 may collectively perform the processing in FIG. 13 for an input acoustic signal having a certain reproduction period (for example, one piece of music content), or it may repeat the processing for each predetermined reproduction period of the input acoustic signal (for example, every 100 ms). Alternatively, the signal processing apparatus 10 may continuously perform modulation processing on an input acoustic signal, such as modulation by analog signal processing, and output a modulated acoustic signal. The processing shown in FIG. 13 may end according to a specific end condition (for example, the passage of a certain period of time, the user's operation, or the output history of modulated sound reaching a predetermined state).

(2-4) Summary

As described above, the signal processing apparatus 10 of the second embodiment acquires an auxiliary acoustic signal having periodic fluctuations corresponding to the frequency of gamma waves, and generates an output acoustic signal based on the auxiliary acoustic signal and the input acoustic signal. As a result, the amplitude of the output acoustic signal can be increased or decreased in a predetermined cycle while allowing the user to experience the sound of the input acoustic signal.

Furthermore, the sound output device 30 may make the user (for example, a dementia patient, a person with pre-dementia, or a healthy person who expects to prevent dementia) listen to a sound according to such an output acoustic signal. This induces gamma waves in the user's brain due to variations in the amplitude of the auxiliary acoustic signal. As a result, the effect of improving the user's cognitive function (for example, treating or preventing dementia) can be expected.

The auxiliary acoustic signal may be a signal having pulses with an interval corresponding to the frequency of the gamma waves. This allows the auxiliary acoustic signal to be generated by simple hardware or processing.

The amplitude of the pulses included in the auxiliary acoustic signal may vary according to the amplitude of the input acoustic signal. This suppresses the adverse effect of the component corresponding to the frequency of the gamma wave on the acoustic experience based on the input acoustic signal, thereby making it easier for the user to listen to the component.

(3) Other Modifications

The storage device 11 may be connected to the signal processing apparatus 10 via the network NW. The display 21 may be built in the signal processing apparatus 10.

In the description of the first embodiment above, an example of modulating at least one acoustic signal included in the intermediate acoustic signal based on the input acoustic signal was shown. However, an output acoustic signal may be generated based on an input acoustic signal and a modulated acoustic signal not derived from the input acoustic signal.

In the above description, an example in which the modulation function has a frequency between 35 Hz and 45 Hz has been mainly described. However, the modulation function used by the signal processing apparatus 10 is not limited to this, and any modulation function that affects the induction of gamma waves in the brain of the listener may be used. For example, the modulation function may have frequencies between 25 Hz and 140 Hz. For example, the frequency of the modulating function may change over time, and the modulating function may have a frequency below 35 Hz or a frequency above 45 Hz in part.

In the above description, the case where the output acoustic signal generated by the signal processing apparatus 10 is output to the sound output device 30 that emits a sound corresponding to the output acoustic signal for the user to hear has been described. However, the output destination of the output acoustic signal by the signal processing apparatus 10 is not limited to this. For example, the signal processing apparatus 10 may output the output acoustic signal to an external storage device or information processing apparatus via a communication network or by broadcasting. At this time, the signal processing apparatus 10 may output the input acoustic signal that has not been modulated together with the output acoustic signal generated by the modulation processing to an external device.

As a result, the external device can arbitrarily select and reproduce one of the unmodulated acoustic signal and the modulated acoustic signal.

Further, the signal processing apparatus 10 may output information indicating the detail of modulation processing to an external device together with the output acoustic signal. Information indicating the detail of modulation processing includes, for example, any of the following:

Information indicating the sound source corresponding to the modulated target signal;

Information indicating the channel corresponding to the modulated target signal;

Information indicating characteristics of the modulated target signal;

Information indicating the modulation function;

Information indicating the degree of modulation; and

Information indicating volume.

Thereby, the external device can change the reproduction method of the acoustic signal according to the detail of the modulation processing.

Further, when the signal processing apparatus 10 acquires additional information (for example, an ID3 tag in an MP3 file) together with the input acoustic signal, the signal processing apparatus 10 may change the additional information and output it to the external device together with the output acoustic signal.

Modifications 1 and 2 have described examples in which different degrees of modulation are applied to different acoustic signals. However, it is also possible to apply different modulation functions to different acoustic signals.

In the second embodiment, an example of synthesizing the adjusted auxiliary acoustic signal with the input acoustic signal has been described. However, the adjusted auxiliary acoustic signal may be synthesized with any of the acoustic signals described in the first embodiment or each modification. As an example, the output acoustic signal may be output after synthesizing the adjusted auxiliary acoustic signal. The acoustic signal to be synthesized with the adjusted acoustic signal (hereinafter "base acoustic signal") may be, for example, the input acoustic signal, the intermediate acoustic signal, the modulated acoustic signal, or the output acoustic signal. Further, when the input acoustic signal, the intermediate acoustic signal, the modulated acoustic signal, or the output acoustic signal includes a plurality of acoustic signals, all of these acoustic signals may be used as the base acoustic signal, or only some of them may be used as the base acoustic signal. In this modification, the amplitude of the auxiliary acoustic signal can be adjusted according to changes in the amplitude of the base acoustic signal.

The second embodiment has exemplified the adjustment of the auxiliary acoustic signal based on the input acoustic signal. However, instead of adjusting the auxiliary acoustic signal, the signal processing apparatus 10 may switch whether to synthesize the auxiliary acoustic signal based on the input acoustic signal. As a first example, when the amplitude of the input acoustic signal exceeds or falls below the threshold, the auxiliary acoustic signal may be synthesized with the input acoustic signal. As a second example, when the period during which the amplitude of the input acoustic signal exceeds the first threshold value or the period during which the amplitude of the input acoustic signal is below the second threshold value exceeds the third threshold value, the auxiliary acoustic signal may be synthesized with the input acoustic signal.

In the above-described embodiment, the case where the acoustic system including the signal processing apparatus 10 is used as a cognitive function improvement system for improving cognitive function (for example, treatment or prevention of dementia) has been mainly described. However, the application of the signal processing apparatus 10 is not limited to this. Literature 1 discloses that when 40-Hz sound stimulation induces gamma waves in the brain, amyloid p is reduced and cognitive function is improved. That is, by making the user hear the sound corresponding to the output acoustic signal output by the signal processing apparatus 10, the amount of amyloid p in the brain of the user is reduced and the deposition is suppressed. It is expected to be useful for the prevention or treatment of various diseases caused by increased amyloid p or deposition of amyloid p. Diseases caused by deposition of amyloid p include, for example, cerebral amyloid angiopathy (CAA). CAA is a disease in which amyloid p protein deposits on the walls of small blood vessels in the brain, making the walls of blood vessels fragile and causing cerebral hemorrhage and the like. As with dementia, there is no therapeutic drug for CAA itself, so the technology described in the above embodiments can be an innovative therapeutic method. That is, the acoustic system 1 comprising the signal processing apparatus 10 and the sound output device 30 for allowing the user to hear a sound corresponding to the output acoustic signal output by the signal processing apparatus 10 can also be used as a medical system for treatment or prevention of cerebral amyloid angiopathy.

According to the above disclosure, the amplitude of an acoustic signal can be varied while reducing degradation of the acoustic experience.

Although the embodiments of the present invention are described in detail above, the scope of the present invention is not limited to the above embodiments. Further, various improvements and modifications can be made to the above embodiments without departing from the spirit of the present invention. In addition, the above embodiments and modifications can be combined.

REFERENCE SIGNS LIST

1: Acoustic system
10: Signal processing apparatus
11: Storage apparatus
12: Processor
13: Input/output interface
14: Communication interface
21: Display
30: Sound output device
50: Sound source device
What is claimed is:
1. A signal processing apparatus, comprising:
a memory that stores instructions; and
a processor that executes the instructions stored in the memory to
receive an input acoustic signal;
acquire a first acoustic signal having periodic variations corresponding to a frequency of a gamma wave by amplitude-modulating a partial signal of the input acoustic signal, the partial signal having a predetermined characteristic;
acquire a second acoustic signal from the input acoustic signal; and
output an output acoustic signal based on the acquired first acoustic signal and the acquired second acoustic signal to induce gamma waves in a brain of a user.
2. The signal processing apparatus according to claim 1, wherein
the first acoustic signal is generated by amplitude-modulating the partial signal of the input acoustic signal using a modulation function with a frequency between 35 Hz and 45 Hz, and wherein
the first acoustic signal has an amplitude change corresponding to a frequency between 35 Hz and 45 Hz.
3. The signal processing apparatus according to claim 1, wherein the partial signal is an acoustic signal corresponding to a sound of a predetermined sound source type.
4. The signal processing apparatus according to claim 1, wherein
the partial signal is an acoustic signal corresponding to a sound that is audible to a listener from a predetermined direction.
5. The signal processing apparatus according to claim 1, wherein
the partial signal is an acoustic signal corresponding to a sound in a predetermined frequency band.
6. The signal processing apparatus according to claim 1, wherein
the partial signal is an acoustic signal corresponding to a sound in a predetermined time period.
7. The signal processing apparatus according to claim 1, wherein
the second acoustic signal is an acoustic signal obtained by separating the first acoustic signal from the input acoustic signal.
8. The signal processing apparatus according to claim 1, wherein
the first acoustic signal is a signal having pulses with an interval corresponding to the frequency of gamma wave.
9. The signal processing apparatus according to claim 8, wherein
the amplitude of the pulse included in the first acoustic signal varies according to an amplitude of the input acoustic signal.
10. The signal processing apparatus according to claim 1, wherein
the output acoustic signal has an amplitude change corresponding to a frequency between 35 Hz and 45 Hz.
11. The signal processing apparatus according to claim 1, wherein
the input acoustic signal is an audio signal including music content.
12. A signal processing method, comprising:
receiving an input acoustic signal;
acquiring a first acoustic signal having periodic variations corresponding to a frequency of a gamma wave by amplitude-modulating a partial signal of the input acoustic signal, the partial signal having a predetermined characteristic;
acquiring a second acoustic signal from the input acoustic signal; and
outputting an output acoustic signal based on the acquired first acoustic signal and the acquired second acoustic signal to induce gamma waves in a brain of a user.
13. The signal processing method according to claim 12, wherein
the first acoustic signal is generated by amplitude-modulating the partial signal of the input acoustic signal using a modulation function with a frequency between 35 Hz and 45 Hz, and wherein
the first acoustic signal has an amplitude change corresponding to a frequency between 35 Hz and 45 Hz.
14. The signal processing method according to claim 12, wherein
the first acoustic signal is a signal having pulses with an interval corresponding to the frequency of gamma wave.
15. A non-transitory computer-readable recording medium that stores a program which causes a computer to execute a method comprising:

receiving an input acoustic signal;

acquiring a first acoustic signal having periodic variations corresponding to a frequency of a gamma wave by amplitude-modulating a partial signal of the input acoustic signal, the partial signal having a predetermined characteristic;

acquiring a second acoustic signal from the input acoustic signal; and outputting an output acoustic signal based on the acquired first acoustic signal and the acquired second acoustic signal to induce gamma waves in a brain of a user.

16. The non-transitory computer-readable recording medium according to claim 15, wherein the first acoustic signal is generated by amplitude-modulating the partial signal of the input acoustic signal using a modulation function with a frequency between 35 Hz and 45 Hz, and wherein the first acoustic signal has an amplitude change corresponding to a frequency between 35 Hz and 45 Hz.

17. The non-transitory computer-readable recording medium according to claim 15, wherein the first acoustic signal is a signal having pulses with an interval corresponding to the frequency of gamma wave.

18. The signal processing apparatus according to claim 1, wherein the second acoustic signal is generated by amplitude-modulating a second partial signal of the input acoustic signal, and wherein the second acoustic signal has an amplitude change corresponding to the frequency of the gamma wave, and wherein a modulation degree of the second acoustic signal is different from a modulation degree of the first acoustic signal.

19. The signal processing apparatus according to claim 1, wherein the processor executes the instructions to determine a degree of modulation based on characteristics of the input acoustic signal, and wherein the amplitude-modulating is performed with the determined degree of modulation.

20. The signal processing method according to claim 12, further comprising causing the user to hear a sound corresponding to the output acoustic signal for cognitive function improvement, wherein the signal processing method is used for improving cognitive function of the user.

* * * * *